(12) United States Patent
Berlinger et al.

(10) Patent No.: US 10,448,905 B2
(45) Date of Patent: *Oct. 22, 2019

(54) FRAMELESS PRE-POSITIONING FOR RADIOSURGERY

(71) Applicant: Brainlab AG, Munich (DE)

(72) Inventors: Kajetan Berlinger, Munich (DE); Stephan Froehlich, Aschheim (DE); Eva Maria Gronbach, Rosenheim (DE)

(73) Assignee: BRAINLAB AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/058,674

(22) Filed: Aug. 8, 2018

(65) Prior Publication Data

US 2018/0344265 A1 Dec. 6, 2018

Related U.S. Application Data

(63) Continuation of application No. 15/118,724, filed as application No. PCT/EP2014/052932 on Feb. 14, 2014, now Pat. No. 10,045,744.

(51) Int. Cl.
*A61B 6/04* (2006.01)
*G06T 7/00* (2017.01)
(Continued)

(52) U.S. Cl.
CPC ............ *A61B 6/0492* (2013.01); *A61B 90/39* (2016.02); *A61N 5/1049* (2013.01);
(Continued)

(58) Field of Classification Search
CPC ........... A61B 6/00; A61B 6/04; A61B 6/0492; A61B 6/52; A61B 6/5211; A61B 6/54;
(Continued)

(56) References Cited

U.S. PATENT DOCUMENTS 6,405,072 B1   6/2002 Cosman
6,501,981 B1  12/2002 Schweikard et al.
(Continued)

FOREIGN PATENT DOCUMENTS

WO   WO2010145711   12/2010

OTHER PUBLICATIONS

International Search Report issued in Application No. PCT/EP2014/052932 dated Oct. 1, 2014.
(Continued)

*Primary Examiner* — Anastasia Midkiff
(74) *Attorney, Agent, or Firm* — Middleton Reutlinger

(57) ABSTRACT

The presently described method is directed to determining a way of positioning a patient before execution of a medical procedure involving irradiating the patient with ionizing treatment radiation based on comparing medical images of the patient with a pre-acquired medical image. The planning computed tomography is searched for an image of the reference structure in order to determine the position of the patient relative to a patient support device. A retroreflective marker device, having a known and advantageously fixed position relative to the base plate, is detected by a navigation system operatively coupled to a motor of the support device. Based on the detected position of the marker device, the motor of the support device is activated to drive the patient into a desired position relative to beam direction along which the treatment radiation is to be issued towards the patient to execute the medical procedure.

14 Claims, 2 Drawing Sheets

(51) Int. Cl.
| | |
|---|---|
| A61N 5/10 | (2006.01) |
| G01T 7/00 | (2006.01) |
| G06K 9/62 | (2006.01) |
| G06K 9/00 | (2006.01) |
| G06K 9/20 | (2006.01) |
| G06K 9/32 | (2006.01) |
| G06T 7/73 | (2017.01) |
| A61B 90/00 | (2016.01) |
| A61B 6/03 | (2006.01) |
| A61B 6/00 | (2006.01) |
| A61B 34/20 | (2016.01) |
| A61B 90/10 | (2016.01) |
| A61B 90/14 | (2016.01) |
| G06F 19/00 | (2018.01) |

(52) U.S. Cl.
CPC ............ *A61N 5/1069* (2013.01); *G01T 7/005* (2013.01); *G06F 19/00* (2013.01); *G06K 9/00208* (2013.01); *G06K 9/2063* (2013.01); *G06K 9/3216* (2013.01); *G06K 9/6212* (2013.01); *G06T 7/0014* (2013.01); *G06T 7/74* (2017.01); *A61B 6/032* (2013.01); *A61B 6/0421* (2013.01); *A61B 6/501* (2013.01); *A61B 6/5211* (2013.01); *A61B 6/547* (2013.01); *A61B 90/14* (2016.02); *A61B 2034/2055* (2016.02); *A61B 2090/101* (2016.02); *A61B 2090/364* (2016.02); *A61B 2090/3937* (2016.02); *A61B 2090/3983* (2016.02); *A61N 2005/1061* (2013.01); *G06K 9/2054* (2013.01); *G06K 9/32* (2013.01); *G06K 2009/2045* (2013.01); *G06K 2009/3225* (2013.01); *G06K 2009/3291* (2013.01); *G06T 2207/10081* (2013.01); *G06T 2207/20221* (2013.01); *G06T 2207/30004* (2013.01); *G06T 2207/30204* (2013.01); *G06T 2207/30208* (2013.01); *G06T 2219/2004* (2013.01)

(58) Field of Classification Search
CPC ........... A61B 6/547; A61B 6/58; A61B 6/589; A61B 90/39; A61B 2090/101; A61B 2090/364; A61B 2090/397; A61B 2090/3937; A61B 2090/3983; A61B 2576/00; A61B 2576/02; A61N 5/10; A61N 5/1048; A61N 5/1049; A61N 5/1064; A61N 5/1069; G01T 7/005; G06K 9/00201; G06K 9/00208; G06K 9/20; G06K 9/2054; G06K 9/2063; G06K 9/32; G06K 9/3216; G06K 9/3233; G06K 9/6212; G06K 9/78; G06K 2009/2045; G06K 2009/3225; G06K 2009/3291; G06K 2209/05; G06K 2209/053; G06K 2209/055; G06K 2209/057; G06K 2207/00; G06K 2207/10; G06K 2207/10072; G06K 2207/10116; G06K 2207/10124; G06K 2207/20; G06K 2207/20112; G06K 2207/20121; G06K 2207/20221; G06K 2207/30; G06K 2207/3004; G06K 2207/30204; G06K 2207/30408

See application file for complete search history.

(56) References Cited

U.S. PATENT DOCUMENTS

| | | |
|---|---|---|
| 7,889,906 B2 | 2/2011 | Smith et al. |
| 10,045,744 B2 * | 8/2018 | Berlinger ............ A61N 5/1069 |
| 2002/0120986 A1 | 9/2002 | Erbel et al. |
| 2013/0287167 A1 | 10/2013 | Gum et al. |
| 2015/0254859 A1 | 9/2015 | Parikh et al. |
| 2017/0215823 A1 | 8/2017 | Ivanov et al. |

OTHER PUBLICATIONS

Wilbert, et al. "Semi-robotic 6 degree of freedom positioning for intracranial high precision radiotherapy; first phantom and clinical results" Radiation Oncology. London, England. May 26, 2010.

* cited by examiner

FRAMELESS PRE-POSITIONING FOR RADIOSURGERY

The present invention relates to a method, in particular a data processing method, of determining positioning control data describing a positioning procedure for positioning an anatomical body part of a patient. The invention also relates to a corresponding computer program and a computer running that program as well as a treatment device comprising such a computer. Furthermore, the invention relates to a medical processing method of executing treatment data which is based on the data processing method of determining positioning control data.

When conducting a navigated medical procedure for in particular tumor therapy such as radiotherapy or radiosurgery, it is commonly necessary to pre-position the patient relative to a source of treatment radiation. A known approach for doing so is to generate a planning computed tomography of the anatomical body part of a patient which is to be irradiated with treatment radiation and, after placing the patient on the bed used for conducting the medical procedure, placing an array of markers in the vicinity of the patient and generating a stereo-x-ray-image of the respective anatomical body part. Thereby, the spatial relationship between the anatomical body parts to be treated (also called treatment body part within the framework of this disclosure) and the array of markers becomes known. Preferably, the markers are trackable using a navigation system which operates on the basis of detecting reflected infrared radiation, and further positioning of the treatment body part relative to the source of treatment radiation may be conducted based on tracking the retroreflective markers while moving the bed and therefore the patient.

However, placing the array of markers in particular onto the patient and around his face involves an additional step in the workflow and may also create a feeling of constriction for the patient.

U.S. Pat. No. 7,889,906 B2 and Wilbert et al., Semirobotic 6 degree of freedom positioning for intracranial high precision radiotherapy. First phantom and clinical results, Radiation Oncology (London, England), 2010 May 26; DOI: 10.1186/1748-717X-5-42 are of general relevance to the field of the present invention.

A problem to be solved by the present invention is to provide a data processing method for pre-positioning of the patient which is more efficient and avoids negative sensations for the patient.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention shall primarily be used in particular within the ExacTrac® frameless radiosurgery system provided by Brainlab AG. The ExacTrac® frameless radiosurgery system offers highly accurate delivery of single- or multi-fraction treatment without a conventional, invasive head ring. A patient-friendly head-to-shoulder mask facilitates a streamlined workflow, overcoming the restrictions of frame-based radiosurgery and improving scheduling flexibility for imaging, planning and treatment. The Using the ExacTrac® frameless radiosurgery system has the following advantages:

- Highly accurate delivery of SRS (stereotactic radiosurgery) without the need to employ a conventional head ring.
- Possible use of a precise non-invasive stereotactic mask system designed for re-producible conformity.
- The procedure can be carried out in time-saving, patient friendly manner without compromising treatment accuracy.

EXEMPLARY SHORT DESCRIPTION OF THE PRESENT INVENTION

In the following, a short description of specific features of the present invention is given which shall not be understood to limit the invention only to the features or a combination of the features described in this section.

The present invention relates in one aspect to a method such as a data processing method embodied by a computer program. This method is directed to determining a way of positioning a patient before execution a medical procedure involving irradiating the patient with ionizing treatment radiation (such as in radiosurgery or radiotherapy) based on comparing medical images such as a planning computed tomography (CT) of the patient (which is acquired with the patient lying on the couch of a treatment apparatus for planning the envisaged medical procedure, i.e. before the medical procedure is carried out) with a pre-acquired medical image. The pre-acquired medical image preferably is a computed tomography (CT) of (advantageously only) a reference structure such as a base plate of head rest onto which the patient's head is to be placed. The planning computed tomography is searched for an image of the reference structure in order to determine the position of the patient (in particular his head) relative to the base plate. After placing the patient onto the couch immediately before treatment, a retroreflective marker device (which is configured to reflect infrared radiation) having a known and advantageously fixed position relative to the base plate is detected by a navigation system operatively coupled to a motor of the couch. The detected position of the marker device is used as a proxy, i.e. as a hint, for the position of the reference structure, and thus, based on information gathered from the planning computed tomography, for the position of the patient (in particular of e.g. his head). Based on the detected position of the marker device, the motor of the couch is activated to drive the patient (in particular his head) into a desired position relative to beam direction along which the treatment radiation is to be issued towards the patient to execute the medical procedure. This is part of a pre-positioning procedure for positioning the patient as required to apply the medical procedure.

The invention also relates to a computer configured to execute the aforementioned computer program, and to a navigation system comprising such a computer. The computer is preferably operatively coupled to the motor of the couch to issue control signal to the motor for driving the couch and thus positioning the patient.

GENERAL DESCRIPTION OF THE PRESENT INVENTION

In this section, a description of the general, in particular preferred, features of the invention is given.

In order to solve the aforementioned problem, in particular a data processing method, particularly a medical data processing method (i.e. a data processing method for use in a medical environment), of determining positioning control data is provided. The positioning control data describes in particular a positioning procedure for positioning an anatomical body part of a patient. The positioning is in particular a pre-positioning of the anatomical body part before a medical procedure is carried out on the patient (in particular on the anatomical body part). The medical procedure is at least one of cranial radiosurgery and radiotherapy. Both cranial radiosurgery and radiotherapy involve irradiating the patient (in particular the anatomical body part) with for example ionizing treatment radiation in particular to influence the tissue properties of a target region such as tissue of a malign tumour.

The method is preferably constituted to be executed by a computer. In particular, it is constituted to be at least partly executed by a computer, i.e. all the steps or merely some of the steps (i.e. less than the total number of steps) of the method in accordance with the invention can be, and in particular are, executed by a computer. The inventive method comprises the following preferred steps and features.

Preferably, reference medical image data is acquired which describes (in particular defines, more particularly represents and/or is) a reference image representation of a reference structure. In particular the image defined by the reference medical image data is an image representation (i.e. a reference image representation) of the reference structure. The reference structure preferably is a patient support device which preferably contains (in particular consists of) a carbon material. In particular, the reference structure is a patient support device such as headrest, in particular the base plate of a head rest. This avoids having to use a localizing device as is known in the state of the art. Such a localizing device may take the shape of a frame in which the anatomical body part (for example the head) can be in particular fixedly positioned with a predetermined spatial relationship relative to the localizing device. Using such a frame in many cases leads to uncomfortable feelings for the patient. The spatial relationship between the reference structure and the marker device preferably is predetermined (in particular known) and advantageously fixed. Within the framework of this disclosure, the term of spatial relationship encompasses at least one of position and orientation. When the anatomical body part is placed on the patient support device, it preferably attains a predetermined, in particular known, spatial relationship relative to the patient support device.

Preferably, the reference medical image data does not describe (in particular not define, more particularly is not and/or does not comprise) an image representation (i.e. an image) of the anatomical body part. In particular, the reference medical image data was generated preferably before the method disclosed herein is executed. In particular. The reference image medical data was generated by imaging the reference structure without imaging the anatomical body part. In particular, the reference image representation is an image of the reference structure in an "empty" state. For example, the reference image representation is an image of the aforementioned patient support device without the anatomical body part being placed on it.

Preferably, patient medical image data is acquired which describes (in particular defines, more particularly represents and/or is) a patient image representation (i.e. a patient image) of the anatomical body part and the reference structure. The anatomical body part comprises in particular at least part of at least one of the head (in particular of the brain) and the neck. The reference medical image data has preferably been generated (in particular before execution of the disclosed method) by applying an x-ray-based imaging modality, in particular a computed tomography imaging modality, to the reference structure. Likewise, the patient medical image data has preferably been generated (preferably before execution of the disclosed method) by applying an x-ray-based imaging modality, in particular a computer tomography imaging modality, to the anatomical body part. The patient medical image data therefore describes (in particular defines, more particularly represents and/or is) preferably a computer tomography image of the anatomical body part. In particular, this computer tomography image is a planning CT which is used to plan the medical procedure to be carried out on the patient.

The position of the reference structure in the patient image representation is preferably detected by fusing the reference image representation (in particular the image defined by the reference medical image data) to the patient image representation (in particular to the image defined by the medical image data). The respectively used fusion algorithm preferably is a rigid fusion algorithm. Such an algorithm is robust enough to reliably fuse the reference image representation of the reference structure to the patient image representation of the reference structure. Thereby, the position of the reference structure in the image defined by the patient medical image data can be determined.

Preferably, treatment position data is acquired which describes (in particular defines, more particularly represents and/or is) a predetermined treatment position of the anatomical body part which it shall attain for conducting the envisaged medical procedure. The treatment position is in particular the position of the anatomical body part which has been planned for properly conducting the medical procedure such as radiosurgery or radiotherapy. In particular, the treatment position defines the position of the anatomical body part relative to the beam of treatment radiation with which the medical procedure is conducted. The treatment position can be defined in a reference system such as a global reference system in which the envisaged medical procedure is planned. For example, the treatment beam (i.e. beam of treatment radiation) may move relative to this reference system (also called planning reference system). The planning reference system in particular is a three-dimensional coordinate system which can be defined in Cartesian coordinates or spherical coordinates. Anyway, even if the treatment position is defined in the planning reference system and the position of the treatment beam is also defined in the planning reference system, the treatment position at least indirectly describes (in particular defines) the position of the anatomical body part relative to the treatment beam. The treatment position is predetermined in particular in the sense that it is determined before execution of the disclosed method, in particular when the envisaged medical procedure is planned.

Preferably, marker reference position data is acquired which describes (in particular defines, more particularly represents and/or is) a predetermined spatial relationship between a marker device and the reference structure. The marker device comprises preferably at least one marker device which is in particular a retroreflective marker device. For example, the at least one marker device is a spherical marker device. The marker device may be disposed on the reference structure, in particular on a patient support device as described above. The spatial relationship between the marker device and the reference structure is preferably known to the disclosed method and in particular fixed.

Preferably, actual marker position data is acquired which describes (in particular defines, more particularly represents and/or is) the actual (in particular current) position of the marker device which it attains in particular during execution of the disclosed method. The actual position of the marker device is in particular the actual position of the marker device in the planning reference system. The actual position of the marker device is acquired preferably based on detecting electromagnetic reflection signals from the surface of the marker device with a detection unit of a navigation system (for example with a stereoscopic camera) and assigning a position in the planning reference system to each reflection signal detected from the marker device. The actual position of the marker device thus is in particular the position of the marker device which it has while the patient is being pre-positioned for the envisaged medical procedure.

Preferably, body part reference position data is determined which describes (in particular defines, more particularly represents and/or is) the spatial relationship between the anatomical body part and the reference structure. The body part reference position data is determined preferably based on the reference medical image data and the patient medical image data. In particular, a transformation between the position of the reference structure and the position of the anatomical body part is determined (in particular computed).

Within the framework of this disclosure, the term of transformation encompasses in particular a mapping such as a linear transformation between positions in (i.e. coordinates) or bases of positional reference systems (coordinate systems) which can be described by a matrix multiplication function which advantageously is linear. The matrix may take the shape of a one-dimensional or a two-dimensional or a three-dimensional matrix or a matrix of even higher dimensionality, depending in particular on the dimensionality of the positions or reference system(s) to be considered, and possibly depending on the information to be regarded such as for example time or number of degrees of freedom.

For example, the reference image representation and the patient image representation are segmented from the reference medical image data and the patient medical image data, respectively. The image representation (i.e. image) of the reference structure is searched for in the patient image representation based on the reference image representation segmented from the reference medical image data. Thus, the position of the reference structure in the patient image representation can be determined, and based on the segmentation of the anatomical body part from the patient image representation, the spatial relationship between the anatomical body part and the reference structure as described by the patient image representation can be determined. Based on this information, the body part reference position data is then determined by applying a basic vector algebra.

Preferably, body part marker position data is determined which describes (in particular defines, more particularly represents and/or is) the spatial relationship between the anatomical body part and the marker device. The body part marker position data is determined preferably based on the body part reference position data and the marker reference position data. Since the spatial relationship between the anatomical body part and the reference structure is known from the body part reference position data determined in the preceding step of the disclosed method, and since the spatial relationship between the marker device and the reference structure is known from the predetermined marker reference position data, the spatial relationship between the anatomical body part and the marker device can be determined by applying basic vector algebra, in particular by determining (for example computing) a coordinate transformation from the spatial relationship of the anatomical body part relative to the reference structure and the spatial relationship between the reference structure and the marker device.

Preferably, positioning control data is determined which describes (in particular defines, more particularly represents and/or is) a positioning procedure for positioning the anatomical body part. The positioning control data is determined preferably based on the treatment position data and the marker reference position data and the body part marker position data. In particular, the marker reference position data and the body part marker position data serve as a basis for determining the spatial relationship between the anatomical body part and the reference structure based on the spatial relationship between the anatomical body part and the marker device defined by the body part marker position data and based on the spatial relationship between the marker device and the reference structure defined by the marker reference position data. Thus, the reference structure which at least indirectly defines the position of the anatomical body part can be positioned (in particular moved) while its position is being tracked by detecting the marker device having a known spatial relationship relative to the reference structure. Since the spatial relationship between the anatomical body part and the marker device is also known, this leads to knowledge about the position of the anatomical body part while moving the reference structure. The positioning control data is then preferably determined by comparing the thus defined position of the anatomical body part to the treatment position defined by the treatment position data. The positioning control data preferably describes (in particular defines) control signals to be issued to a moving unit for moving a support device, in particular a couch, on which the anatomical body part and/or the patient is placed. These control signals in particular are defined such that they instruct the moving unit to move the anatomical body part and/or the patient such that the position of the anatomical body part is moved towards the treatment position and advantageously becomes equal to the treatment position if it is determined that the position of the anatomical body part is not equal to the treatment position. The moving unit is therefore instructed to move the anatomical body part and/or the patient according to the positioning procedure which includes in particular at least one of a translational and a rotational movement of the anatomical body part and/or the support device on which the anatomical body part and/or the patient is placed in at least one respectively translational or rotational degree of freedom.

The above-described method therefore allows to conduct a positioning procedure for positioning the anatomical body part ready for treatment based on detecting a known reference image representation of a reference structure in a medical image containing a patient image representation of the anatomical body part and the reference structure and based on tracking a marker device having a known spatial relationship relative to the reference structure. It is no longer necessary to use a localizer device such as a frame placed over the head of the patient conduct the positioning procedure. Rather, the reference structure may be embodied by any other (physical and/or tangible and/or structural) entity appearing in the reference image representation and the patient image representation and having a predetermined (in particular known) spatial relationship relative to the marker device.

The positioning procedure is to be carried out before the envisaged medical procedure is carried out. Further preferably, the positioning procedure is carried out without carrying out the envisaged medical procedure, in particular without carrying out any step relating to or encompassing treatment of the human or animal body by surgery or therapy.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or in particular comprise or encompass any surgical or therapeutic activity. The invention is instead directed in particular to positioning the tool relative to the medical implant, which may be outside the patient's body. For this reason alone, no surgical or therapeutic activity and in particular no surgical or therapeutic step is necessitated or implied by carrying out the invention.

The invention in another aspect also relates to a data processing method (in particular medical data processing method) of executing treatment data describing (in particular defining, more particularly representing and/or being) a treatment to be carried out on a patient. This method is preferably also constituted to be executed by a computer and comprises the following preferred steps:

a) executing the above-described method of determining positioning control data;
b) acquiring the treatment data and executing the treatment data based on the patient medical image data and the reference medical image data.

Execution of the treatment data is done in particular based on identifying the patient image representation of the reference structure in the image described (in particularly defined, more particularly represented) by the patient medical image data. For example, it is determined whether the reference structure has a position which defines a proper (i.e. desired) position (in particular the treatment position) of the anatomical body part as described above, and, if this is the case, the treatment data is executed. The treatment data in particular describe treatment control signal to be issued to a treatment unit for treating the patient's body such as a particle accelerator or high-energy x-ray tube such that the treatment beam is activated.

The treatment data describes (in particular defines, more particularly represents and/or is) in particular treatment parameters such as at least one of a treatment dose to be applied to the anatomical body part by irradiating it with treatment radiation, and a treatment position. The treatment position considers in particular an allowed deviation from a planned irradiation direction, i.e. from a predetermined direction of the treatment beam which is defined preferably in the planning reference system.

The method of executing treatment data preferably also comprises a step of comparing the reference medical image data to the patient medical image data. The treatment data is preferably executed if the comparison results in that the reference structure described by the patient image representation is the same as the reference structure described by the reference image representation. This comparison is carried out in particular based on the reference image representation segmented from the reference medical image data and the patient image representation of the reference structure.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, in particular electrical, in particular technically generated) signal wave, in particular a digital signal wave, carrying information which represents the program, in particular the aforementioned program, which in particular comprises code means which are adapted to perform any or all of the method steps described herein.

The invention also relates to a treatment device which may be in particular an irradiation device such as a radiosurgery device or radiotherapy device. The treatment device comprises in particular the aforementioned computer on which a program is running or into the memory of which a program is loaded which, when running on the computer or when loaded onto the computer, causes the computer to perform the method steps described herein. The treatment device preferably also comprises a medical imaging unit such as an x-ray device for acquiring the patient medical image data. The medical image unit can be a stereo-x-ray device or an x-ray-based computer tomograph (CT) or a magnetic resonance tomograph (MRT).

The computer of the treatment device is preferably operatively coupled to the medical imaging unit to issue control signals to the medical imaging unit for acquiring the patient medical image data. Furthermore, the computer is preferably operatively coupled to the above-described moving unit for moving the support device on which the anatomical body part and/or the patient is placed.

The invention provides in particular the advantage of not having to use additional marker devices which are opaque for x-rays and which are disposed in or on the reference structure such as the above-described patient support device. Rather, preferably the carbon material of the patient support device such as a head rest for the head and at least part of the neck is used to image the reference structure based on application of an x-ray-based imaging modality. It is noted that carbon material is opaque for x-rays and allows to generate an image of the reference structure which is free of artefacts.

It is within the scope of the present invention to combine one or more features of one or more embodiments in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can in particular be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand. The transmitter preferably emits electromagnetic radiation in the infrared wavelength band which is reflected from the marker device. The receiver such as a stereoscopic camera detects these reflections and forwards corresponding signals to the computer which converts these reflection signals into positions in a reference system such as the planning reference system.

The present invention relates to the field of medicine and in particular to the use of beams, in particular radiation beams, to treat parts of a patient's body, which are therefore also referred to as treatment beams. A treatment beam treats body parts which are to be treated and which are referred to in the following as "treatment body parts". These body parts are in particular parts of a patient's body, i.e. anatomical body parts. Ionising radiation is in particular used for the purpose of treatment. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, in particular the treatment beam, is in particular used in radiation therapy or radiotherapy, in particular in the field of oncology. For treating cancer in particular, parts of the body comprising a pathological structure or tissue such as a tumour are treated using ionising radiation. The tumour is then an example of a treatment body part.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body.

The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. Analytical devices in particular are used to generate the image data in apparatus-based imaging methods. The imaging methods are in particular used for medical diagnostics, to analyse the anatomical body in order to generate images which are described by the image data. The imaging methods are also in particular used to detect pathological changes in the human body. However, some of the changes in the anatomical structure, in particular the pathological changes in the structures (tissue), may not be detectable and in particular may not be visible in the images generated by the imaging methods. A tumour represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. MRI scans represent an example of an imaging method.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the World Wide Web (WWW) and located in a so-called cloud of computers which are all connected to the World Wide Web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (World Wide Web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are in particular designed to enable a seamless transition from one dataset (for example a first dataset such as for example a first image) to another dataset (for example a second dataset such as for example a second image). The transformation is in particular designed such that one of the first and second datasets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field. These vectors are determined by the optimisation algorithm in such a way as to result in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). These constraints include in particular the constraint that the transformation is regular, which in particular means that a Jacobian determinant calculated from a matrix of the deformation field (in particular, the vector field) is larger than zero, and also the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than one tenth or one hundredth or one thousandth of the diameter of the image, and in particular about equal to or less than the distance between neighbouring voxels. Large deformations can be implemented, in particular due to a high number of (iteration) steps.

The determined elastic fusion transformation can in particular be used to compare the first and second datasets (first and second images), in particular to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can in particular be determined on the basis of a determined correlation between the first and second datasets.

DESCRIPTION OF THE FIGURES

In the following, an example embodiment of the invention will be described with reference to the figures, wherein the invention shall not be limited to the features described in connection with the figures, and wherein.

Figure 1:
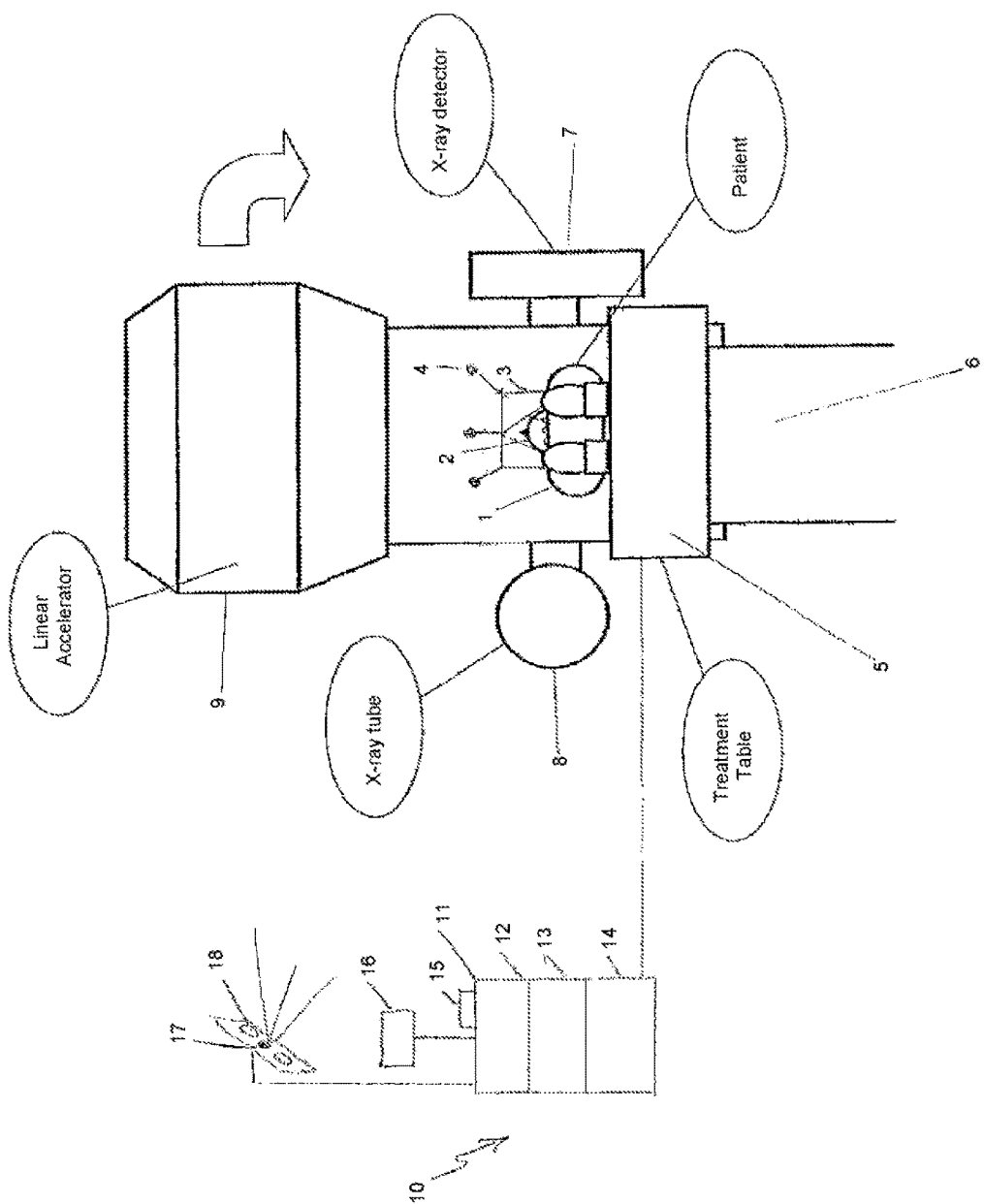
FIG. 1 shows a treatment device usable for conducting the invention.

According to FIG. 1, the treatment device (which can be a radiotherapy or radiosurgery device) comprises at least a patient support device embodied by a treatment table 5, an imaging unit comprising an x-ray tube 8 and an x-ray detector 7, and a treatment unit embodied by a linear accelerator 9 which is configured to emit a treatment beam comprising ionizing treatment radiation onto the anatomical body part represented by the patient's head 2. A patient 1 having the anatomical body part is placed on the patient support device embodied by the treatment table 5 which can be moved by a moving unit embodied by an electric motor 6. The treatment table 5 is placed under the treatment unit. The curved arrow indicates that the linear accelerator 9 can be rotated around the patient's longitudinal axis. A headrest 3 made from a carbon material is placed adjacent to (in particular under) the patient's head in order to keep the position of the patient's head relative to the linear accelerator 9 in a fixed and predetermined position. The base plate of the headrest 3 is shown in FIG. 1 out of perspective and merely for reasons of illustration. A marker device comprising a plurality of markers 4 is disposed on the headrest 3, in the case of FIG. 1 three markers 4a used. The spatial relationship between the markers 4 and the headrest 3 is known and fixed. The treatment device also comprises a computer 11 which is part of a navigation system 10. The computer 11 comprises a volatile memory such as a RAM 14, a non-volatile memory embodied by a hard disc 13 and a processing unit embodied by microprocessor 12. Furthermore, the computer 11 is operatively coupled to an input unit embodied by a keyboard 15 and a visual output unit such as a monitor 16. The navigation system also comprises a transmitter of the navigation system embodied by infrared transmitters 17 and a receiver embodied by infrared-sensitive stereoscopic camera 18 which are both operatively coupled to the computer 11. The computer 11 is also configured to control the other parts of the treatment device such as the imaging unit and the treatment unit and the moving unit.

Figure 2:
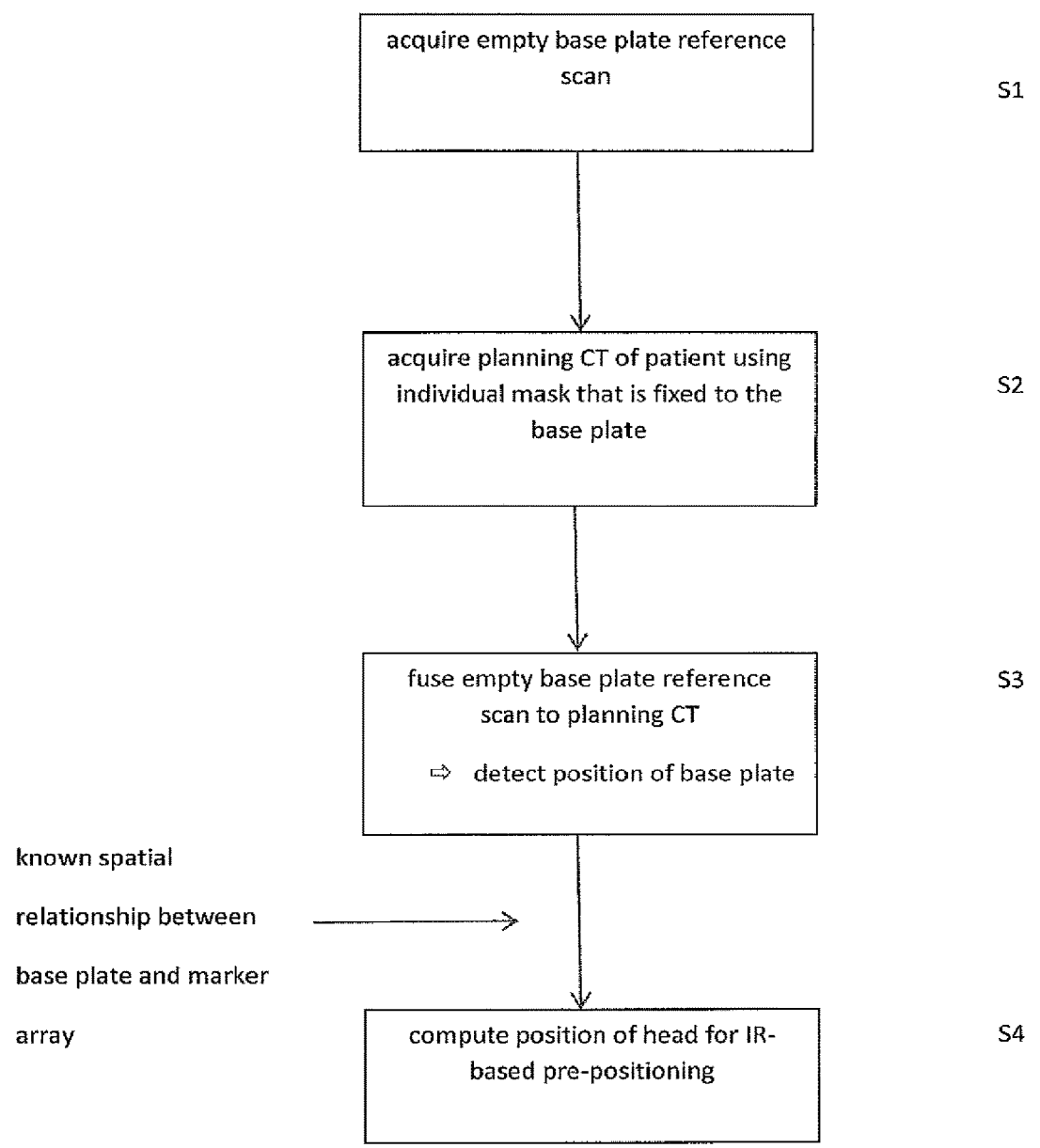
FIG. 2 is a flow diagram showing the functionality of the method in accordance with the invention.

FIG. 2 shows a flow diagram comprising the basic steps of the disclosed method. In step S1, the reference medical image data is acquired by acquiring an empty baseplate reference scan of the empty baseplate of the headrest 3. In step S2, a planning CT of the patient 1 is acquired which embodies acquisition of the patient medical image data. The planning CT is acquired while an individual mask for fixing the patient on the headrest 3 is fixed to the headrest 3, in particular to the base plate. In step S3, the empty base plate reference scan is fused to the planning CT to detect the position of the base plate in the planning CT. Step S3 thus represents the above-described step of determining the position of the reference structure in the image defined by the patient medical image data. Based on the known spatial relationship between the base plate and the marker array (array of markers 4, i.e. the aforementioned marker device), the position of the patient's head 2 can be computed for pre-positioning of the head 2 before radiosurgery or radiotherapy is executed by activating the linear accelerator 9. The pre-positioning is conducted based on detecting, with the camera 18, infrared signals reflected from the marker array and thus is also called IR-based pre-positioning. The positioning of the head is effected by moving the treatment table 5 on which the patient 1 is placed. This movement is conducted by issuing control signals describing the pre-positioning from the computer 11 to the motor 6 which then moves the treatment table 5.

The invention claimed is:

1. A medical system for positioning a patient for treatment, comprising
   a computer configured to issue control signals to a medical imaging unit for acquiring the patient medical image data, and wherein the computer is configured for sending control signals to a patient support device on which the anatomical body part and/or the patient is placed;
   the computer configured to be communicatively connected to the patient support device;
   the computer having a memory and processor wherein the memory has instructions thereon, the instructions, when executed by the processor of the computer, determine positioning control data describing a positioning procedure for positioning an anatomical body part of a patient by the patient support device, the instructions, when executed by the computer, further implementing the steps of:
   acquiring, at the processor, reference medical image data describing a reference image representation of a reference structure;
   acquiring, at the processor, the patient medical image data describing a patient image representation of the anatomical body part and the reference structure;
   acquiring, at the processor, treatment position data describing a predetermined treatment position of the anatomical body part which it shall attain for conducting a medical procedure;
   acquiring, at the processor, marker reference position data describing a predetermined spatial relationship between a marker device and the reference structure;
   acquiring, at the processor, actual marker position data describing the actual position of the marker device;
   determining, by the processor and based on the reference medical image data and the patient medical image data, body part reference position data describing the spatial relationship between the anatomical body part and the reference structure;
   determining, by the processor and based on the body part reference position data and the marker reference position data, body part marker position data describing the spatial relationship between the anatomical body part and the marker device;
   determining, by the processor and based on the treatment position data and the marker reference position data and the body part marker position data, positioning control data describing a positioning procedure for positioning the anatomical body part, wherein the reference medical image data does not describe an image representation of the anatomical body part;
   sending a control signal to the patient support device according to the position control data.

2. A computer-implemented method of determining a positioning procedure for positioning an anatomical body part of a patient by positioning a patient support device, the method comprising executing, on a processor of a computer, the steps of:
   acquiring, at the processor, reference medical image data describing a reference image representation of a reference structure;
   acquiring, at the processor, patient medical image data describing a patient image representation of the anatomical body part and the reference structure;
   acquiring, at the processor, treatment position data describing a predetermined treatment position of the anatomical body part which it shall attain for conducting a medical procedure;
   acquiring, at the processor, marker reference position data describing a predetermined spatial relationship between a marker device and the reference structure;
   acquiring, at the processor, actual marker position data describing the actual position of the marker device;
   determining, by the processor and based on the reference medical image data and the patient medical image data, body part reference position data describing the spatial relationship between the anatomical body part and the reference structure;
   determining, by the processor and based on the body part reference position data and the marker reference position data, body part marker position data describing the spatial relationship between the anatomical body part and the marker device;
   determining, by the processor and based on the treatment position data and the marker reference position data and the body part marker position data, positioning control data describing a positioning procedure for positioning the anatomical body part, wherein the reference medical image data does not describe an image representation of the anatomical body part, wherein the reference medical image data does not describe an image representation of the anatomical body part;

transmitting position control data for moving the patient support device according to the positioning procedure.

3. The method according to claim 2, wherein reference medical image data has been
generated by applying an x-ray-based imaging modality f to the reference structure and wherein the patient medical image data has been generated by applying an x-ray-based imaging modality to the anatomical body part.

4. The method according to claim 2, wherein the envisaged medical procedure is at least
one of radiosurgery and radiotherapy which is to be applied to the anatomical body part and wherein the treatment position is a position in which the anatomical body part is to be irradiated with treatment radiation.

5. The method according to claim 2, wherein the positioning procedure is to be carried out before the medical procedure is carried out.

6. The method according to claim 2, wherein the marker device comprises at least one marker.

7. The method according to claim 2, wherein the anatomical body part comprises at least part of at least one of the head and the neck.

8. The method according to claim 2, wherein the reference structure is a patient support device which contains a carbon material wherein the marker device is disposed relative to the patient support device at a predetermined position.

9. The method according to claim 2, wherein the positioning procedure includes at least one of a translational and a rotational movement of the anatomical body part.

10. The method according to claim 2, wherein the positioning control data describes control signals to be issued to a moving unit for moving a support device on which the anatomical body part or the patient is placed according to the positioning procedure.

11. The method according to claim 2 further including:
acquiring, at the processor, the treatment data and executing the treatment data based on the patient medical image data and the reference medical image data for example based on identifying the reference structure in the patient image representation.

12. The method according to the claim 11, wherein the treatment data describes treatment parameters including at least one of the treatment dose to be applied and the treatment position.

13. The method according to claim 11, further including:
comparing, by the processor, the reference medical image data to the patient medical image data, wherein the treatment data is executed if the comparison results in that the reference structure described by the patient image representation is the same as the reference structure described by the reference image representation.

14. A non-transitory computer-readable storage medium storing a computer program which, when executed on at least one processor of at least one computer, cause the computer to determine control data positioning an anatomical body part of a patient on a patient support device, the computer program having instructions which when executed on the at least one processor, cause the at least one processor to:

acquire, at least one processor, reference medical image data describing a reference image representation of a reference structure;

acquire, at the at least one processor, patient medical image data describing a patient image representation of the anatomical body part and the reference structure;

acquire, at the at least one processor, treatment position data describing a predetermined treatment position of the anatomical body part which it shall attain for conducting a medical procedure;

acquire, at the least one processor, marker reference position data describing a predetermined spatial relationship between a marker device and the reference structure;

acquire, at the at least one processor, actual marker position data describing the actual position of the marker device;

determine, by the at least once processor and based on the reference medical image data and the patient medical image data, body part reference position data describing the spatial relationship between the anatomical body part and the reference structure;

determine, by the at least once processor and based on the body part reference position data and the marker reference position data, body part marker position data describing the spatial relationship between the anatomical body part and the marker device;

determine, by the at least one processor and based on the treatment position data and the marker reference position data and the body part marker position data, positioning control data describing a positioning procedure for positioning the anatomical body part, wherein the reference medical image data does not describe an image representation of the anatomical body part, wherein the reference medical image data does not describe an image representation of the anatomical body part;

transmit position control data for moving the patient support device according to the positioning procedure.

* * * * *